United States Patent [19]

Sorgenfrey

[11] Patent Number: 6,152,379
[45] Date of Patent: Nov. 28, 2000

[54] COMPOSITION FOR AIR TREATMENT DISPENSERS PROVIDING A LONG LASTING, CONSTANT EMANATING COMPOSITION

[75] Inventor: Dirk Sorgenfrey, Caldwell, N.J.

[73] Assignee: Dragoco Gerberding & Co. AG, Germany

[21] Appl. No.: 09/307,224

[22] Filed: May 7, 1999

[51] Int. Cl.$^7$ .......................................................... A61L 9/04
[52] U.S. Cl. .................................. 239/6; 239/34; 239/44; 239/47; 239/49; 422/5; 422/123; 422/305; 512/1; 512/3
[58] Field of Search .................................... 239/6, 34, 44, 239/47, 49, 50, 145; 422/4, 5, 123, 125, 305, 306; 512/1, 2, 3

[56] References Cited

U.S. PATENT DOCUMENTS

| | | | |
|---|---|---|---|
| 4,286,754 | 9/1981 | Jones | 239/44 X |
| 4,419,326 | 12/1983 | Santini | 422/123 X |
| 4,445,641 | 5/1984 | Baker et al. | 239/6 |
| 4,663,315 | 5/1987 | Hasegawa et al. | 239/44 X |
| 4,948,047 | 8/1990 | Zembrodt | 239/34 |
| 5,081,104 | 1/1992 | Orson, Sr. | 239/44 X |
| 5,534,229 | 7/1996 | Nomura et al. | 422/5 X |
| 5,746,019 | 5/1998 | Fisher | 239/47 X |

*Primary Examiner*—Andres Kashnikow
*Assistant Examiner*—Steven J. Ganey
*Attorney, Agent, or Firm*—Pendorf & Cutliff

[57] ABSTRACT

Two associated air treatment compositions are formulated such that when used together they produce a constant emanating composition throughout the life of an air treatment dispenser of the wick type (dispenser). Composition I comprises components (at least two active agents) in their respective intended concentrations and is used to impregnate the evaporation surface and/or wick of the dispenser. Composition II comprises the same components (at least the same two active agents) as the first composition. However, the concentrations of the components in Composition II with respect to Composition I are adjusted such that a constant emanating composition is maintained. The relationship between Composition I and II can be described by equation $$X_{i;0} = \frac{100 * c_i X_{i;\infty}}{\sum_{i=1}^{m} c_i X_{i;\infty}},$$

where $$\sum_{i=1}^{m} X_{i;0}$$

is composition II and $$\sum_{i=1}^{m} X_{i;\infty}$$

is composition I. Coefficients $c_i$ can be calculated based on quantitative analysis of composition I and II by means known in the art. Composition II serves as a replenishing fluid, typically provided in a reservoir, with which the wick is in contact.

10 Claims, 2 Drawing Sheets

COMPOSITION FOR AIR TREATMENT DISPENSERS PROVIDING A LONG LASTING, CONSTANT EMANATING COMPOSITION

FIELD OF THE INVENTION

The present invention relates to a system for treating air using a wick type dispenser and at least two air treatment compositions having different formulations. More specifically, one of the two compositions is used to impregnate or wet the wick and/or evaporation surface of the wick type air treatment dispenser, while the corresponding second composition serves as a replenishing fluid, typically provided in a reservoir, with which the wick and/or evaporation surface is in contact.

The compositions can be formulated to release vapors of active ingredients such as air-freshener aromatics, medicaments, decongestants, inhalants, repellants, insecticides, bactericides, deodorants, and the like, at a uniform rate and for a sustained period of time.

BACKGROUND OF THE ART

The use of dispensers for air treatment, which utilize capillary action, typically by means of a wick, to draw volatile liquid materials from a reservoir isolated from the atmosphere to a surface from which said volatile liquid materials can emanate into the atmosphere, have long been known in the art. Wicking devices are described in U.S. Pat. Nos. 1,994,932; 2,597,195; 2,802,695; 3,550,853; 4,286754; 4,323,193; 4,413,779; 4,454,987; 4,739,928; 4,913,350; 5,000,383; 5,749520; and 5,875,968; incorporated by reference.

For further discussion "emanating composition" is defined as the composition located immediately at the evaporative surface, i.e. it constitutes the composition which can be olfactively perceived. This is in contrast to the composition in the reservoir, which for definition purposes can be called "reservoir composition".

Dispensers of the prior art operate well for single component liquids or multi-component liquids, which form an azeotropic mixture. However, liquids having multiple components of differing volatility cannot be disseminated from prior art dispensers, without a change in emanating composition during the life of the dispenser. The change in the emanating composition is typically reflected by a reduction in weight loss per time unit during the life of the dispenser, as the less volatile components of the liquid accumulate at the evaporative surface, thus progressively lowering the overall vapor pressure (Raoult's Law). This is also commonly referred to as wick blockage. Since the composition in the reservoir essentially remains the same, there is an increasing discrepancy between the composition in the reservoir and the emanating composition, which evolves at the evaporative surface during the life of the dispenser.

With respect to fragrance compositions intended for air treatment this is a formidable problem. Typically, fragrance compositions are very complex mixtures of components having vastly different vapor pressures. The greater the difference in vapor pressure among the components, the more obvious will be the change in the emanating composition. E.g. this is especially true for lemon notes, which typically contain a high concentration of rather volatile components (top notes). The challenge for the perfumer then becomes to create a fragrance composition, which not only provides a balanced and pleasant emanating composition initially, but which remains balanced and pleasant despite the progressive changes during the life of the dispenser.

Changes in odor character are less of a problem for notes, which do not require a high amount of top notes, because the emanating composition does not change as drastically. Yet, less volatile components still accumulate on the evaporation surface relative to more volatile components, so that the emanating composition becomes less impactful, i.e. the air freshener becomes weaker over time.

Examples of prior art suggesting solutions to this and related problems are as follows: Bjorksten (U.S. Pat. No. 2,529,536, issued on Nov. 14, 1950) proposes to invert the wick periodically to keep it from clogging up. Bulloff (U.S. Pat. No. 2,905,591, issued on Sept. 22, 1959) as well as Ohara et al. (U.S. Pat. No. 3,903,022, issued on Sept. 2, 1975) teach the use of materials of similar vapor pressure; Similarly, Lazier (U.S. Pat. No. 2,710,825, issued on Jun. 14, 1955) teaches the exclusion of highly volatile components to impart a more constant odor character during the life of a dispenser. Lanzet (U.S. Pat. No. 2,927,055, issued on Mar. 1, 1960) recommends the use of a gelling agent in water to equalize the evaporation rates of components of a liquid, which are otherwise dissimilar. Sekiguchi et al. (U.S. Pat. No. 3,679,133, issued on Jul. 25, 1972) teach the use of pressure in lieu of a wicking action to deliver volatile liquids to an evaporation surface. Miller/Miller et al. (U.S. Pat. Nos. 5,749,519, issued on May 12, 1998 and U.S. Pat. No. 5,875,968, issued on Mar. 2, 1999) utilize the non-porous wicking action of a dual container, where the sidewalls are in a capillary spacing proximity, to deliver liquids to an evaporation surface. Compton et al. (U.S. Pat. No. 4,323, 193, issued on Apr. 6, 1982) teach the use of an evaporation matrix which has a very large surface compared to the weight of liquid it can hold. In addition, the authors suggest limiting the amount of very volatile components to less than 25%, while the amount of low volatility components should be limited depending on the wick holding capacity.

Either these approaches limit the choice of components to those of similar volatility or they attempt to defy the physics of the liquid to be evaporated, since any composition having components of very different volatility will gradually change into an emanating composition with less components of high volatility and more components of low volatility during the life of the dispenser.

Sullivan et al. (U.S. Pat. No. 4,158,440, issued on Jun. 19, 1979) teach to group components of a liquid according to their volatility and to dispense each group by a separate dispensing means. This approach provides a more constant emanating composition over a long time period, even if the original liquid comprises components of different volatilities. However, within each group, the less volatile components increase in concentration over time relative to the more volatile components. Moreover, using multiple separate dispensers may be less economical than a single dispenser. Finally, the group comprising the most volatile components could exhibit a dangerously low flash point.

De Laire (U.S. Pat. No. 4,413,779, issued on Nov. 8, 1983) teaches impregnation of the evaporation surface with an agent, the evaporation rate of which is chosen, relative to the rate of deposition of the less volatile components of the air treating composition, to result in an even dispersion rate over a desired operating period. This approach addresses the problem of decreasing weight loss per time unit associated with air treatment dispensers of the wick type, but fails to eliminate the gradual change the emanating composition undergoes.

There remains a need for a well designed air treatment composition, which can deliver a constant emanating composition throughout the entire life of the dispenser without any limitations to the choice of components with respect to their volatility.

Accordingly, it is an object of this invention to provide a constant emanating air treatment composition throughout the life of an air treatment dispenser of the wick type.

It is another object of the invention to provide two corresponding air treatment compositions; one of the two compositions is used to impregnate the wick of the air treatment dispenser of the wick type, while the corresponding second composition serves as a replenishing fluid, typically provided in a reservoir, which the wick is in contact with.

It is a further object of the invention to provide a mathematical equation, which describes the relationship between the two corresponding air treatment compositions.

Other objects and advantages of the present invention shall become apparent from the accompanying detailed description of the invention.

SUMMARY OF THE INVENTION

Two associated air treatment compositions are formulated such that when used together they produce a constant emanating composition throughout the life of an air treatment dispenser of the wick type (dispenser). Composition I comprises components (at least two active agents) in their respective intended concentrations and is used to impregnate the evaporation surface and/or wick of the dispenser. Composition II comprises the same components (at least the same two active agents) as the first composition. However, the concentrations of the components in Composition II with respect to Composition I are adjusted such that a constant emanating composition is maintained. This is accomplished by typically increasing the concentration of the more volatile components and decreasing the concentration of the less volatile components in Composition II.

The relationship between Composition I and II can be described by equation $$X_{i;0} = \frac{100 * c_i X_{i;\infty}}{\sum_{i=1}^{m} c_i X_{i;\infty}},$$

where $$\sum_{i=1}^{m} X_{i;0}$$

is composition II and $$\sum_{i=1}^{m} X_{i;\infty}$$

is composition I.

Coefficients $c_i$ can be calculated based on quantitative analysis of composition I and II by means known in the art. Composition II serves as a replenishing fluid, typically provided in a reservoir, with which the wick is in contact.

Since the dispenser is designed to be refilled, it can be used over and over again, and thus it becomes practical to manufacture the dispenser of materials having higher value than materials typically used in the manufacture of disposable dispensers. Thus, the invention makes it possible on the one hand to provide in the home an attractive porcelain or clay air treatment dispenser, and on the other hand reduces waste associated with disposable and non-recyclable articles. The dispenser of the present invention thus has value as a decorative or gift item which properties are not associated with disposable articles.

DETAILED DESCRIPTION OF THE INVENTION

Figure 1:
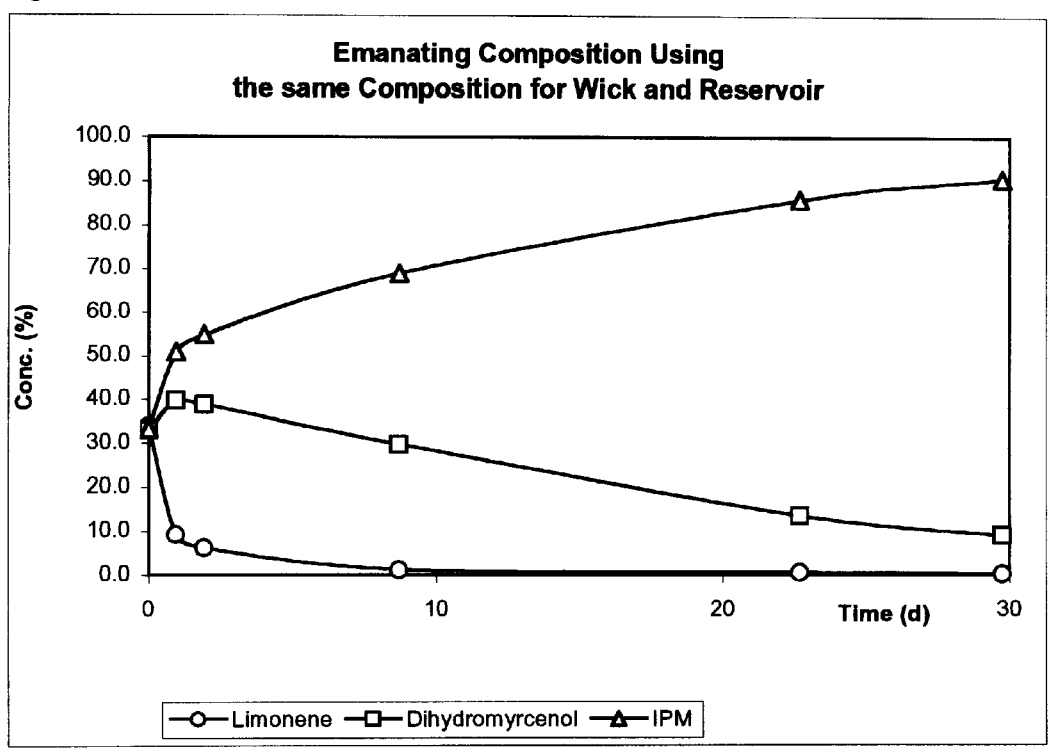
FIG. 1 shows the change in emanating composition (see definition in BACKGROUND OF THE ART) of a three component mixture. The components differ vastly in volatility, showing typical but exaggerated results for illustrative purposes.

What follows is a detailed description of the present invention, and particularly a description of the preferred embodiments, which constitute the best mode of carrying out the present invention. This description exemplifies the present invention, but is not intended to limit the scope of the invention, which is delineated in the claims, which conclude the specification.

In order to appreciate the present invention, a mathematical model will be discussed, which describes the change in emanating composition typically encountered in air treatment dispensers of the wick type. As an air freshening composition reaches the surface of a wick, its individual components evaporate according to their partial vapor pressure, which is basically described by Raoult's Law. Since the partial vapor pressure of each volatile component is essentially unique, there are components, which volatilize more quickly than others; from another perspective, some components stay on the wick surface longer than others. Therefore, less volatile components accumulate on the wick surface over the lifetime of a wick type air freshener, which results in a change in the emanating composition.

Any portion of the air freshening composition, which evaporates from the surface of the wick, is replaced by the air freshening composition from the reservoir. The composition of the air freshening composition in the reservoir essentially remains unchanged during the life of the air treatment dispenser, because the wick provides its only relevant contact with the atmosphere; see

TABLE 1

Table 1: Effect of Wick Treatment on Evaporation of D-Limonene (%)

| | Weight (%) | |
|---|---|---|
| | Initial | Day 7 |
| Wick untreated | 100.0 | 11.9 |
| Wick soaked with IPM | 100.0 | 98.3 |
| Wick soaked with IPM and neck sealed off with petrolatum | 100.0 | 99.0 |
| Closed bottle | 100.0 | 99.0 |

Equation (1) describes this phenomenon. $X_{i;n}$ is the concentration of component (i) of an air freshening composition, containing (m) different components. (n) refers to an unspecified time interval, after which a certain fraction of $X_i$ namely $c_i$, has evaporated from the surface of the wick. The first term of Equation (1) refers to the loss to evaporation $[X_{i;n}(1-c_i)]$. The second term quantifies the amount of $X_i$ that wicks to the surface of the wick. The sum of all evaporated fractions of all components is replaced by the unchanged composition, of which $X_i$ constitutes a certain percentage.

Equation (1):
$$X_{i;n+1} = X_{i;n}(1-c_i) + \frac{X_{i;0}}{100}\sum_{i=1}^{m} c_i X_{i;n} \quad \begin{array}{l} X_{i;n} \leq 100\%; c \leq 1; \\ i = (1, \ldots, m); m, n = N_o \end{array}$$

After the time interval (n) has elapsed indefinite times (n=∞), at which point (n) equals (n+1), the concentrations of the components reach an equilibrium on the surface of the wick. Equation (2) describes the equilibrium:

Equation (2):
$$X_{i;\infty} = \frac{X_{i;0}}{c_i(100 - X_{i;0})}\sum_{j=1}^{m} c_j X_{j;\infty} \quad \begin{array}{l} X_{i;n} \leq 100\%; c \leq 1; \\ i \neq j; i, j = (1, \ldots, m); m = N_o \end{array}$$

When (n) equals infinity, Equation (1) can be solved for $X_{i;0}$, which is the initial concentration (n=0). This is depicted by Equation (3):

Equation (3):
$$X_{i;0} = \frac{100 * c_i X_{i;\infty}}{\sum_{i=1}^{m} c_i X_{i;\infty}} \quad X_{i;n} \leq 100\%; c \leq 1;$$

$$i = (1, \ldots, m); m = N_o$$

The above equations relate to the prior art, specifically to fragrance compositions, as follows: A perfumer would cremate an air freshening composition, which can be described mathematically as $$\sum_{i=1}^{m} X_{i;0}(A),$$

where $X_{i;0}$ is the concentration of component (i) of an air freshening composition, containing (m) different components at time zero. Initially, the composition emanating from the evaporative surface is the same as the composition the perfumer created. During the life of the dispenser, however, the emanating composition changes, even though the replenishing composition in the reservoir is still the same as the one the perfumer created. The emanating composition drifts towards an equilibrium, which can be described mathematically as $$\sum_{i=1}^{m} X_{i;\infty}(B),$$

where $X_{i;\infty}$ is the concentration of component (i) of the emanating composition, containing (m) different components at time infinity. If the change of the odor character from (A) to (B) is noticeable, the perfumer has to make sure, that not only composition (A), the initial composition, is balanced and pleasant. All the compositions, which are transgressed, as composition (A) changes into composition (B), likewise need to be balanced and pleasant.

As discussed earlier, a number of patents teach to avoid the use of components of high volatility, i.e. to minimize top notes, in order to maintain the initial odor character of the emanating composition. However, even if the odor character does not change significantly, as the emanating composition changes from (A) to (B), yet another problem associated with dispensers of the wick type still remains. Less volatile components still accumulate on the evaporation surface relative to more volatile components, so that the emanating composition becomes less impactful, i.e. the air freshener becomes weaker over time.

As discussed earlier, a number of patents teach to use components of similar volatility in order to maintain the initial odor character of the emanating composition. This approach severely limits the choice of components for a perfumer. This approach, too, can be described by one of the above equations, specifically Equation (3). If the volatility rates were the same for all components of an emanating composition, $c_i$ in Equation (3) is the same for all $X_i$. In this case $c_i$ can be factored out from the sum in the denominator. Subsequently, $c_i$ can be canceled out from numerator and denominator. Since $$\sum_{i=1}^{m} X_{i;\infty}$$

constitutes the entire composition at time (t=∞), $$\sum_{i=1}^{m} X_{i;\infty} = 100\%.$$

Then, "100" cancels out from numerator and denominator. What is left is $X_{i;0}=X_{i;\infty}$, which means that (A)=(B).

(A)=(B), i.e. no change in the emanating composition over the life of a dispenser, is the object of this invention. However, unlike prior art, the present invention achieves this objective even for very complex compositions having components of vastly different vapor pressure. This eliminates limitations set forth in the prior art faced by perfumers.

In order to appreciate the present invention, three compositions need to be considered: 1.) the initial emanating composition (A), which is the most desired composition, 2.) the emanating composition at equilibrium (B), as well as 3.) the "replenishing" composition in the reservoir (R). In the prior art, (R) was the same as (A), which causes (B) to be different from (A), unless all components have the same evaporation rate, in which case (A)=(B)=(R). But, for the majority of cases, (A)≠(B) with the above discussed associated problems.

It is well known in the art, that initially the weight loss per time unit is the highest, and that it levels off relatively quickly in context of the intended life of the dispenser. This reflects the fact, that the emanating composition reaches equilibrium relatively early in the life of a dispenser. Therefore, the present invention makes (B) the most desired composition rather than (A). With this approach (R) is still the same as (A), and (B) is still different from (A) at equilibrium for the majority of cases. But since (B) is the odor character, which is perceived the longest during the life of a dispenser, this is a major improvement over the prior art, because it also guaranties, that the emanating composition is satisfactorily strong at equilibrium. The difficulty is, how to determine composition (A).

What follows is a step by step procedure to obtain composition (A).

Step 1: The desired composition is filled into the dispenser intended for the final product.

Step 2: The dispenser is operated until the emanating composition reaches equilibrium, which is indicated by a constant weight loss per time unit.

Step 3: The initial emanating composition, which is the same as the one in the reservoir, as well as the emanating composition at equilibrium need to be quantitatively analyzed by means well known in the art, i.e. gas-chromatography, etc.

Step 4: Based on the data obtained in Step 3, the factors, by which the concentration of each component of the emanating compositions changed, are calculated. These factors are represented by $c_i$ in the above equations.

Step 5: Equation 3 is used.

$$\sum_{i=1}^{m} X_{i;\infty}$$

is equated with the intended composition. Along with the determined values for $c_i$ (see Step 4), $X_{i;0}$ for each component can be calculated. Composition (A) is then equal to $$\sum_{i=1}^{m} X_{i;0}.$$

Step 6: In order to verify, that (A) evolves into the desired composition (B), composition (A) is filled into the dispenser intended for the final product and Step 2 is repeated. The emanating composition at equilibrium is analyzed and compared to the desired composition.

If the data in Step 6 are not satisfactorily closely in agreement, Step 2 through Step 6 are repeated until the data are satisfactory.

In order to provide a constant emanating composition including the time before equilibrium is reached, the evaporation surface/wick is presoaked/impregnated with composition (B) and the reservoir, which the wick is in contact with, should contain composition (A).

EXAMPLE

As an example, a three-component mixture was prepared. The three active agents were selected first, to show that the invention operates even in the case that the active agents differ greatly in evaporation rate, and second, to better illustrate the technical phenomena underlying the present invention. The components and their respective vapor pressure were: Limonene (Limo) 0.9 torr, Dihydromyrcenol (DHM) 0.09 torr, and Isopropyl Myristate (IPM) 0.000 torr. Limo (71.0 g), DHM (69.0 g), and IPM (70.0 g) were weighed out and 100.0 g of this composition was poured into a bottle (reservoir). A wick was pierced through the seal in the bottle neck and brought in contact with the liquid in the reservoir. For sampling (about 0.4 g) the wick was squeezed. Quantitative analysis was done by GC. Samples were taken on day 1, 2, 9, 23, and 30. A sample from the bottle served to determine the initial concentration. FIG. 1 depicts the change in concentration of Limo, DHM, and IPM, respectively, over the course of the life of the "air treatment" dispenser at the surface of the wick, which represents the emanating composition. As expected, IPM quickly accumulates at the wick surface.

Figure 2:
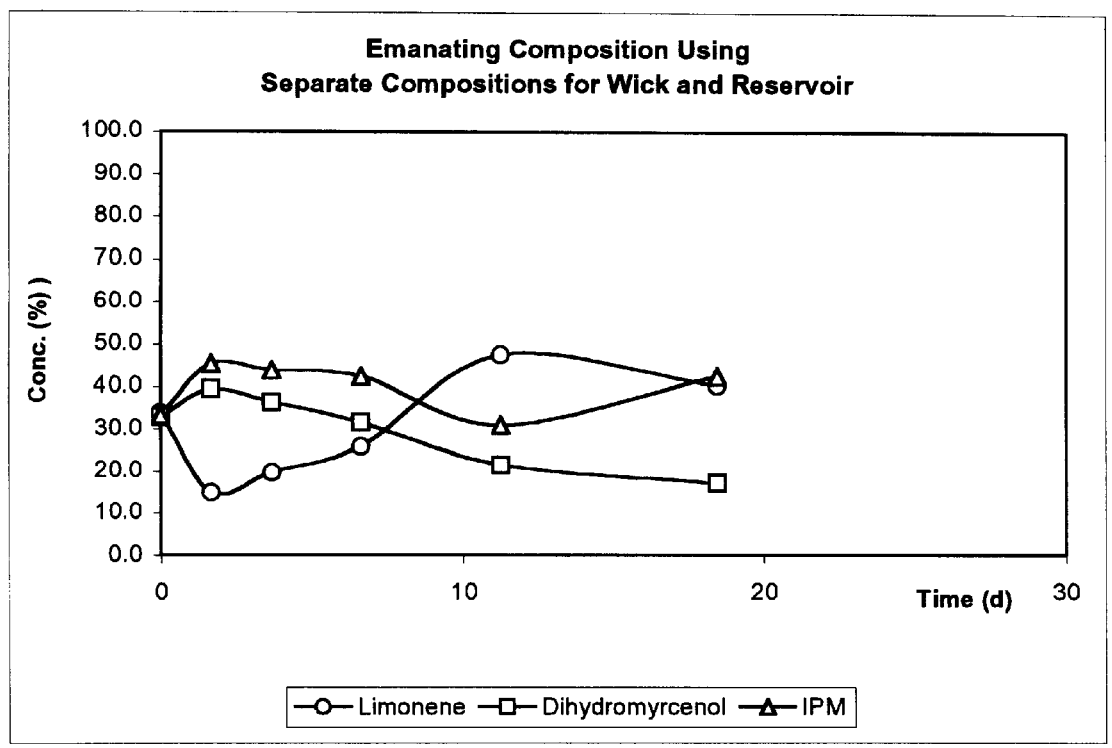
FIG. 2 shows that the emanating composition stays more constant than described in FIG. 1, if two corresponding air treatment compositions are employed for wick and reservoir.

The coefficients $c_i$ were calculated based on the quantitative analysis for Limo, DHM, and IPM, respectively, using a computer model built off Equation (1). Values for $c_i$ were adjusted until the concentrations for Limo, DHM, and IPM in the equation matched the respective concentration obtained by quantitative analysis. $c_i$ were determined to be 0.246 for Limo, 0.016 for DHM, and 0.002 for IPM, respectively. Since $$\sum_{i=1}^{m} X_{i;\infty}$$

in Equation 3 can be equated with Limo (33.8%), DHM (32.9%), and IPM (33.3%), the concentration of the components of the replenishing composition in the reservoir was determined to be as follows: 93.4% Limo, 5.8% DHM, and 0.8% IPM. Next, 100.0 g of the replenishing composition were poured into a bottle (reservoir) and the wick was presoaked with about 15 g of the intended emanating composition (Limonene 33.8%, Dihydromyrcenol 32.9%, and IPM 33.3%). FIG. 2 describes the change in emanating composition as sampled and analyzed on days 2, 4, 7, 11, and 18. The Limonene concentration dropped initially, because it took a while for the replenishing composition to replace the 15 g of the composition, the wick was initially impregnated with. Overall, the emanating composition stayed significantly more constant than that depicted in FIG. 1.

I claim:

1. A method for treating air using a wick type dispenser comprising a reservoir and a wick and/or evaporation surface extending between said reservoir and the air to be treated, said method comprising:
    (a) formulating a first composition comprising at least first and second active agents, said second active agent having a higher evaporation rate than said first active agent;
    (b) formulating a second composition comprising said at least first and second active agents, wherein the ratio of said first active agent to said second active agent in said second composition is lower than the ratio of said first active agent to said second active agent in said first composition;
    (c) treating said wick and/or evaporation surface with said first air treatment composition; and
    providing a supply of said second air treatment composition in said reservoir.

2. A method as in claim 1, wherein said active agents are selected from the group consisting of air-freshener aromatics, medicaments, decongestants, inhalants, repellants, insecticides, bactericides, and deodorants.

3. A method as in claim 1, wherein at least one of said active agents is an air-freshener aromatic.

4. A method as in claim 1, wherein said step of treating said wick with said first air treatment composition comprises wetting less than half of said wick with said first air treatment composition.

5. A method as in claim 1, wherein said step of treating said wick with said first air treatment composition comprises wetting more than half of said wick with said first air treatment composition.

6. A method as in claim 1, wherein said step of treating said wick with said first air treatment composition comprises wetting all of said wick with said first air treatment composition.

7. A method as in claim 1, wherein the vapor pressure of said second active agent is at least 20% greater, measured in torr than the vapor pressure of said first active agent.

8. A replenishing solution for replenishing an in-use wick type dispenser, wherein said in-use wick type dispenser comprises a reservoir and a wick and/or evaporation surface extending between said reservoir and the air to be treated, said wick and/or evaporation surface being provided with an air treating composition comprising at least first and second active agents, said second active agent having a higher evaporation rate than said first active agent; said first and second active agents being present in a desired ratio for emanating said first and second active agents into the air, wherein said replenishing solution comprises at least said first and second active agents such that when said replenishing solution is added to said reservoir the proportion of said second active agent to first active agent is greater in said replenishing solution than in said air treatment composition on said wick and/or evaporation surface.

9. A system for treating air using a wick type air treatment dispenser comprising a reservoir and a wick and/or evaporation surface communicating between said reservoir and the air to be treated, said system employing at least two air treatment compositions, Composition I and Composition II, which two compositions, when used together, result in a constant emanating composition throughout the life of said wick type air treatment dispenser, wherein Composition I and Composition II contain, in different proportions, at least two identical active agents having different evaporative character, said system comprising formulating Composition I to give the desired emanating composition measured at the wick and/or evaporation surface, using Composition I to impregnate or wet the wick and/or evaporation surface of the dispenser, formulating Composition II as a replenishing fluid, and supplying Composition II to said reservoir, wherein the relationship between said Composition I and Composite II is further described by the equation $$X_{i;0} = \frac{100 * c_i X_{i;\infty}}{\sum_{i=1}^{m} c_i X_{i;\infty}},$$

wherein $$\sum_{i=1}^{m} X_{i;0}$$

is Composition II and $$\sum_{i=1}^{m} X_{i;\infty}$$

is Composition I; wherein coefficients $c_i$ can be calculated based on quantitative analysis of Composition I and II.

10. An air treatment dispenser comprising:
    a wick type dispenser comprising a reservoir and a wick and/or evaporation surface extending between said reservoir and the air to be treated, said wick treated with a first air treatment composition comprising at least first and second active agents, said second active agent having a higher evaporation rate than said first active agent, wherein at least said wick is sealed against evaporation; and
    a second air treatment composition comprising at least said first and second active agents, said second composition being provided in said reservoir, wherein the ratio of said first active agent to said second active agent in said second composition is lower than the ratio of said first active agent to said second active agent in said first composition, said reservoir sealed against the atmosphere and against said wick.

* * * * *